United States Patent
Grollier et al.

(10) Patent No.: US 6,258,131 B1
(45) Date of Patent: Jul. 10, 2001

(54) PROCESS FOR PRESERVING THE DYEING CAPACITY OF 5, 6-DIHYDROXYINDOLE AND OF ITS AND DERIVATIVES IN AN AQUEOUS MEDIUM, COMPOSITION AND DYEING PROCESS

(75) Inventors: Jean Francois Grollier, Paris; Marie Francoise Bosq, Clichy; Jean Cotteret, Verneuil-sur-Seine; Arnaud De Labbey, Aulnay-sous-Bois, all of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/947,383

(22) Filed: Oct. 8, 1997

Related U.S. Application Data

(63) Continuation of application No. 08/536,179, filed on Sep. 29, 1995, now abandoned, which is a continuation of application No. 08/390,742, filed on Feb. 17, 1995, now Pat. No. 9,478,360, which is a continuation of application No. 08/041,987, filed on Apr. 2, 1993, now abandoned, which is a continuation of application No. 07/706,194, filed on May 28, 1991, now abandoned, which is a continuation of application No. 07/336,492, filed on Apr. 12, 1989, now abandoned.

(30) Foreign Application Priority Data

Apr. 12, 1988 (LU) .......................................... 87196

(51) Int. Cl.⁷ ..................................................... A61K 7/13
(52) U.S. Cl. ........................................ 8/423; 8/406; 8/604
(58) Field of Search ............................... 8/405, 406, 423, 8/435, 604

(56) References Cited

U.S. PATENT DOCUMENTS

| | | | |
|---|---|---|---|
| 3,194,734 | 7/1965 | Seemuller et al. | 8/423 |
| 3,993,436 | 11/1976 | Fujinuma | 8/424 |
| 4,004,877 | 1/1977 | Saphir | 8/410 |
| 4,013,404 | 3/1977 | Parent et al. | 8/423 |
| 4,129,644 | 12/1978 | Kalopissis et al. | 424/59 |
| 4,208,183 * | 6/1980 | Grollier et al. | 8/409 |
| 4,466,805 | 8/1984 | Welters et al. | 8/406 |
| 4,732,692 | 3/1988 | Zabotto et al. | 510/136 |
| 4,804,385 | 2/1989 | Grollier et al. | 8/423 |
| 4,822,375 | 4/1989 | Lang et al. | 8/423 |
| 4,885,006 | 12/1989 | Grollier et al. | 8/423 |
| 4,888,027 | 12/1989 | Grollier et al. | 8/423 |
| 4,900,326 | 2/1990 | Grollier et al. | 8/409 |
| 5,021,067 * | 6/1991 | Grollier | 8/423 |
| 5,173,085 | 12/1992 | Brown et al. | 8/405 |
| 5,492,541 * | 2/1996 | Murphy et al. | 8/423 |
| 5,516,916 * | 5/1996 | Murphy et al. | 548/509 |

OTHER PUBLICATIONS

Chemical Abstracts, vol. 92, No. 12, Mar. 1980, p. 335, 99441d.

CRC Handbood of Chemistry and Physics, 1983, pp.w D154–D156 (No Month Available).

* cited by examiner

Primary Examiner—Caroline D. Liott
(74) Attorney, Agent, or Firm—Pillsbury Winthrop LLP

(57) ABSTRACT

Process for preserving the dyeing capacity of 5,6-dihydroxyindole or of of its derivatives corresponding to the formula (I);

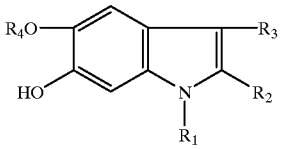

(I)

in which $R_1$, $R_2$, $R_3$ and $R_4$, which are identical or different donates hydrogen or a $C_1$–$C_4$ lower alkyl, $R_1$, $R_2$ and $R_3$ denoting hydrogen when $R_4$ denotes alkyl in an aqueous medium, characterized in that the pH of the aqueous medium is adjusted to a value $pH_C$ of between 5 and 10 by employing a pH-regulating agent containing two components (A) and (B), the component (A) being chosen from pH-regulating agents which have a dissociation constant $K_{CA}$ in aqueous solution at 25° C., such as $pk_{CA}$, that is:

$$0 < pk_{CA} - pH_C \leq 2.5$$

and the component (B) being chosen from pH-regulating agents which have a dissociation constant $K_{CB}$ in aqueous solution at 25° C., such as $pk_{CB}$, that is:

$$2 < pk_{CB} < pH_C.$$

17 Claims, No Drawings

PROCESS FOR PRESERVING THE DYEING CAPACITY OF 5, 6-DIHYDROXYINDOLE AND OF ITS AND DERIVATIVES IN AN AQUEOUS MEDIUM, COMPOSITION AND DYEING PROCESS

This is a continuation of application Ser. No. 08/536,179, filed Sep. 29, 1995, now abandoned, which is a continuation of application Ser. No. 08/390,742, filed Feb. 17, 1995, now U.S. Pat. No. 5,478,360, which is a continuation of application Ser. No. 8/041,987, filed Apr. 2, 1993, now abandoned, which is a continuation of application Ser. No. 07/706,194, filed May 28, 1991, now abandoned, which is a continuation of application Ser. No. 07/336,492, filed Apr. 12, 1989, now abandoned.

Process for preserving the dyeing capacity of 5,6-dihydroxyindole and of its derivatives in an aqueous medium, composition and dyeing process.

The present invention relates to a process for preserving the dyeing capacity of 5,6-dihydroxyindole and of certain derivatives in an aqueous medium, to aqueous dyeing compositions based on 5,6-dihydroxyindole and on its derivatives exhibiting improved dyeing capacity retention properties and to the dyeing process making use thereof.

The color of hair, of the skin and of body hair, particularly of human origin is due chiefly to melanin related pigments secreted by the melanocytes. These pigments, of natural origin, include in particular pigments which are called eumelanins. Their natural biosynthesis takes place in several steps by polymerization of the oxidation products of an amino acid, tyrosine, and one of these oxidation products is 5,6-dihydroxyindole, which in its turn polymerizes to eumelanin.

It has already been proposed in the past to repigment human hair with 5,6-dihydroxyindole, more particularly by employing aqueous 5,6-dihydroxyindole compositions. Hair can be dyed by virtue of such compositions, it being possible for this dyeing to be performed a number of times or progressively, by repigmenting the hair by virtue of this dye to give light shades using one application of the product and to an increasingly intensified shade by superposing the applications.

These compositions are generally adjusted to a pH of between 5 and 10 and more particularly between 7 and 9. However, the Applicant has found that the hair coloring could be impared following the storage of the dye composition based on 5,6-dihydroxyindole in an aqueous medium. It is found, in fact, that after the dyeing composition has been stored for a few weeks or months, the hair shades obtained are modified or impaired when compared with the initial shade.

The applicant have found that, surprisingly, this problem of preserving the dyeing capacity and characteristics of 5,6-dihydroxyindole and of its derivatives in an aqueous medium could be solved by virtue of the use, in the aqueous medium, of an agent containing two components which do not complex the indole-related dye, as an agent enabling the pH to be adjusted.

A subject-matter of the present invention is therefore a process for preserving the dyeing capacity of 5,6-dihydroxyindole and of its derivatives in an aqueous medium by the use of a pH-regulating agent containing two components which do not inhibit the dyeing capacity of the indole-related dye.

Another subject of the invention consists of the dyeing composition based on 5,6-dihydroxyindole and/or on its derivatives containing such a pH-regulating agent and of the dyeing process making use thereof.

Other subjects of the invention will become apparent on reading the description and the examples which follow.

The process for preserving the dyeing capacity of 5,6-dihydroxyindole and/or of its derivatives corresponding to the formula (I):

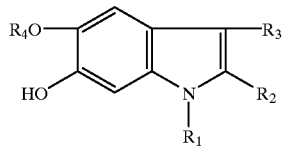

(I)

in which $R_1$, $R_2$, $R_3$ and $R_4$, which are identical or different, denote hydrogen or a $C_1$–$C_4$ lower alkyl, $R_1$, $R_2$ and $R_3$ denoting hydrogen when $R_4$ denotes alkyl in an aqueous medium, in accordance with the invention, is characterized essentially by the fact that, in order to adjust the pH to a value $pH_C$ of between 5 and 10 and preferably between 7 and 9, a pH-regulating agent comprising two components (A) and (B) is employed, the component (A) exhibiting a dissociation constant $K_{CA}$ in aqueous solution at 25° C., such as $pk_{CA}$, that is:

$$0 < pk_{CA} - pH_C < 2.5$$

the component (B) having a dissociation constant $K_{CB}$ in aqueous solution at 25° C., such as $pk_{CB}$, that is:

$$2 < pk_{CB} < pH_C$$

the components (A) and (B) not inhibiting the dyeing capacity of the indole-related dye.

In the formula (I), an alkyl preferably denotes methyl and $R_1$, $R_2$ and $R_3$ do not denote an alkyl simultaneously.

The preferred compounds of formula (I) are chosen from 5,6-dihydroxyindole, 2-methyl-5,6-dihydroxyindole, 3-methyl-5,6-dihydroxyindole, 1-methyl-5,6-dihydroxyindole, 2,3-dimethyl-5,6-dihydroxyindole and 5-methoxy6-hydroxyindole.

A preferred embodiment of the invention consists in employing the component (A) in such proportions that the weight ratio of component (A) to component (B) is higher than 1 and that the molar ratio of component (A) to component (B) is higher than or equal to 2 and lower than 15.

The pH-regulating agent containing two components, employed in accordance with the invention, is employed in proportions which are preferably between $5 \times 10^{-3}$ and $50 \times 10^{-3}$ moles per 100 g of dyeing composition.

The components A and B which are more particularly preferred in the process in accordance with the invention are chosen from the following pairs: triethanolamine ($pk_{CA}$: 4.7)/tartaric acid ($pk_{CB}$: 3.2); dipotassium hydrogen phosphate ($pk_{CA}$: 7.2)/potassium dihydrogen phosphate ($pk_{CB}$: 2.1).

The dyeing compositions for keratinous fibers, in particular for human hair, which form another subject of the present invention are more particularly characterized by the fact that they contain, in a suitable aqueous medium for dyeing, at least 5,6-dihydroxyindole and/or one of its derivatives of formula (I) and a pH-regulating agent which makes it possible to obtain a $pH_C$ having a value of between 5 and 10 and preferably between 7 and 9, this pH-regulating agent comprising two components (A) and (B) which do not complex the indole-related dye and correspond to the definition outlined above.

In the compositions in accordance with the invention, 5,6-dihydroxyindole and/or its derivatives of formula (I) is (are) preferably employed in proportions of between 0.01 and 5% by weight and preferably between 0.03 and 3% by weight relative to the total weight of the composition. The proportions which are particularly preferred are the proportions between 0.2 and 1% by weight and more particularly between 0.3 and 0.9% by weight relative to the total weight of the composition.

These compositions may contain suitable adjuvants for dyeing, which are well known in dyeing compositions and, in the case where these compositions are intended to be applied to hair, these adjuvants are cosmetically acceptable. More particularly, they may contain organic solvents in proportions of 0.5 to 50% by weight and preferably of 2 to 20% by weight relative to the total weight of the composition, these being chosen more particularly from $C_1$–$C_4$ lower alcohols such as ethyl alcohol, propyl alcohol, isopropyl alcohol, tert-butyl alcohol, ethylene glycol, propylene glycol, ethylene glycol monomethyl, monoethyl and monobutyl ethers, ethylene glycol monoethyl ether acetate, propylene glycol and dipropylene glycol monomethyl ethers and methyl lactate. The preferred solvents are chosen more particularly from ethyl alcohol and propylene glycol.

These compositions may be thickened with thickening agents which are preferably employed in proportions by weight of between 0.1 and 5%, in particular between 0.5 and 3% relative to the total weight of the composition. These thickeners are chosen more particularly from sodium alginate, gum arabic, guar gum, heterobiopolysaccharides such as xanthan gum or scleroglucans, cellulose derivatives such as methyl cellulose, hydroxyethyl cellulose and hydroxypropyl methyl cellulose, carboxymethyl cellulose sodium salt and acrylic acid polymers, or else inorganic thickening agents such as bentonite.

These compositions may also contain anionic, cationic, nonionic or amphoteric surface-active agents or mixtures thereof. These surface-active agents are preferably employed in proportions of between 0.1 and 50% by weight relative to the total weight of the composition, and advantageously between 1 and 20% by weight.

Another subject of the invention is a dyeing process making use of a composition of this kind, which is stabilized with time. This process consists in applying the composition such as defined above to keratinous fibers, and in particular to human hair, for an application time of 1 min to 40 min, in following this application with a rinse, a shampoo if desired, a new rinse and drying.

One of the preferred embodiments consists in performing a so-called progressive dyeing consisting in a dyeing composition such as defined above being applied a number of times and successively until the desired shade is obtained.

The following examples are intended to illustrate the invention without being of a limiting nature.

EXAMPLE 1

Natural hair containing 90% of white is dyed by applying the following composition to the hair:

| | |
|---|---|
| 5,6-Dihydroxyindole | 0.5 g |
| Ethyl alcohol | 10 g |
| Xanthan gum sold under the name Rhodopol SC by Rhône-Poulenc | 2 g |
| Glucoside alkyl ether of formula: | 2.1 g AS |

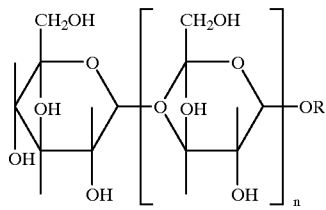

(n = 1 to 5, R denotes $C_8$–$C_{10}$ alkyl)
sold at a concentration of 60% of active substance (AS) under the name Triton CG 110 by Rohm and Haas

| | |
|---|---|
| Triethanolamine | 4 g |
| Tartaric acid | 0.3 g |
| pH:8.5 | |
| Preserving agent | q.s. |
| Water | q.s. 100 g |

The application time is 10 minutes. Conventional shampooing is carried out and the hair is dried.

After three applications of this composition, the hair is dyed a natural middle grey shade, in the same way as when the hair is dyed with an identical composition, but whose pH of 8.5 has been adjusted only with triethanolamine, that is to say without tartaric acid.

After two months at 25° C. and 45° C., the coloring obtained using the first composition in accordance with the invention is unaltered, whereas that obtained with the second composition has undergone a marked alteration and a very marked alteration at 25 and 45° C. respectively.

EXAMPLE 2

Natural hair containing 90% of white is dyed by applying the following composition to the hair:

| | |
|---|---|
| 5,6-Dihydroxyindole | 0.5 g |
| Ethyl alcohol | 10 g |
| Xanthan gum sold under the name Rhodopol SC by Rhône-Poulenc | 2 g |
| Glucoside alkyl ether of formula: | 2.1 g AS |

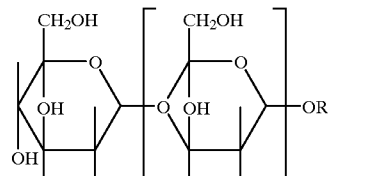

(n = 1 to 5, R denotes $C_8$–$C_{10}$ alkyl)
sold at a concentration of 60% of active substance (AS) under the name Triton CG 110 by Rohm and Haas

| | |
|---|---|
| Dipotassium hydrogen phosphate | 0.87 g |
| Potassium dihydrogen phosphate | 0.30 g |
| pH:7.1 | |
| Preserving agent | q.s. |
| Water | q.s. 100 g |

The application time is 10 minutes. Shampooing is carried out and the hair is then dried.

After three applications of this composition, the hair is dyed a light beige grey shade.

EXAMPLE 3

Natural hair containing 90% of white is dyed by applying the following composition to the hair:

| | |
|---|---|
| 5,6-Dihydroxyindole | 0.8 g |
| Ethyl alcohol | 10 g |
| Xanthan gum sold under the name Rhodopol SC by Rhône-Poulenc | 2 g |
| Glucoside alkyl ether of formula: | 2.1 g AS |

[Structure: (n = 1 to 5, R denotes $C_8$–$C_{10}$ alkyl) sold at a concentration of 60% of active substance (AS) under the name Triton CG 110 by Rohm and Haas]

| | |
|---|---|
| Triethanolamine | 4 g |
| Tartaric acid | 0.3 g |
| pH:8.5 | |
| Preserving agent | q.s. |
| Water | q.s. 100 g |

The exposure time is 10 minutes. Shampooing is carried out and the hair is then dried.

After three applications of this composition the hair is dyed a medium grey shade.

EXAMPLE 4

Natural hair containing 90% of white is dyed by applying the following composition to the hair:

| | |
|---|---|
| 3-Methyl-5,6-dihydroxyindole | 0.2 g |
| Ethyl alcohol | 10 g |
| Xanthan gum sold under the name Rhodopol SC by Rhône-Poulenc | 2 g |
| Glucoside alkyl ether of formula: | 2.1 g AS |

[Structure: (n = 1 to 5, R denotes $C_8$–$C_{10}$ alkyl) sold at a concentration of 60% of active substance (AS) under the name Triton CG 110 by Rohm and Haas]

| | |
|---|---|
| Triethanolamine | 4 g |
| Tartaric acid | 0.3 g |
| pH:8.5 | |
| Preserving agent | q.s. |
| Water | q.s. 100 g |

The application time is 10 minutes. Conventional shampooing is carried out and the hair is then dried.

After three applications the hair is dyed a blue ashen shade.

EXAMPLE 5

Natural hair containing 90% of white is dyed by applying the following composition to the hair:

| | |
|---|---|
| 3-Methyl-5,6-dihydroxyindole | 0.5 g |
| Ethyl alcohol | 10 g |
| Xanthan gum sold under the name Rhodopol SC by Rhône-Poulenc | 2 g |
| Glucoside alkyl ether of formula: | 2.1 g AS |

[Structure: (n = 1 to 5, R denotes $C_8$–$C_{10}$ alkyl) sold at a concentration of 60% of active substance (AS) under the name Triton CG 110 by Rohm and Haas]

| | |
|---|---|
| Triethanolamine | 4 g |
| Tartaric acid | 0.3 g |
| pH:8.5 | |
| Preserving agent | q.s. |
| Water | q.s. 100 g |

The application time is 10 minutes. Conventional shampooing is carried out and the hair is then dried.

After one application the hair is dyed an ashen blue shade which becomes deeper after several applications.

EXAMPLE 6

Natural hair containing 90% of white is dyed by applying the following composition to the hair:

| | |
|---|---|
| 2-Methyl-5,6-dihydroxyindole | 0.5 g |
| Ethyl alcohol | 10 g |
| Xanthan gum sold under the name Rhodopol SC by Rhône-Poulenc | 2 g |
| Glucoside alkyl ether of formula: | 2.1 g AS |

[Structure: (n = 1 to 5, R denotes $C_8$–$C_{10}$ alkyl) sold at a concentration of 60% of active substance (AS) under the name Triton CG 110 by Rohm and Haas]

| | |
|---|---|
| Triethanolamine | 4 g |
| Tartaric acid | 0.3 g |
| pH:8.5 | |
| Preserving agent | q.s. |
| Water | q.s. 100 g |

The application time is 10 minutes. Conventional shampooing is carried out and the hair is then dried.

After one application of this composition the hair is dyed a beige light blond shade.

EXAMPLE 7

Natural hair containing 90% of white is dyed by applying the following composition to the hair:

| | |
|---|---|
| 2,3-Dimethyl-5,6-dihydroxyindole | 0.5 g |
| Ethyl alcohol | 10 g |
| Xanthan gum sold under the name Rhodopol SC by Rhône-Poulenc | 2 g |
| Glucoside alkyl ether of formula: | 2.1 g AS |

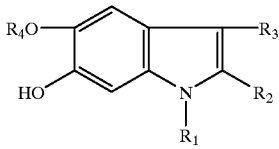

(n = 1 to 5, R denotes $C_8$–$C_{10}$ alkyl)
sold at a concentration of 60% of active
substance (AS) under the name Triton CG 110
by Rohm and Haas

| | |
|---|---|
| Triethanolamine | 4 g |
| Tartaric acid | 0.3 g |
| pH:8.5 | |
| Preserving agent | q.s. |
| Water | q.s. 100 g |

The application time is 10 minutes. Conventional shampooing is carried out and the hair is then dried.

After one application of this composition the hair is dyed an ashen light blond shade.

What is claimed is:

1. A process for preserving the dyeing capacity of a dyeing agent in an aqueous medium, said dyeing agent consisting of an indole, said indole having the formula

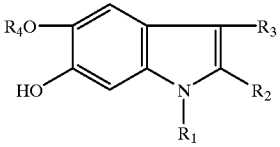

(I)

wherein
$R_1$, $R_2$, $R_3$ and $R_4$, each independently, represent hydrogen or $C_1$–$C_4$ lower alkyl with the proviso that $R_1$, $R_2$ and $R_3$ represent hydrogen when $R_4$ represents alkyl, said process comprising adjusting the pH of said aqueous medium to a $pH_C$ value of between 5 and 10 by adding thereto a pH regulating agent containing two components (A) and (B), said component (A) being triethanolamine and said component (B) being a pH regulating agent having a dissociation constant, $K_{CB}$, in an aqueous solution at 25° C., of $2 < pK_{CB} \leq pH_C$, the weight ratio of said component (A) to said component (B) being greater than 1 and the molar ratio of said component (A) to said component (B) being greater than or equal to 2 and less than 15.

2. The process of claim 1 wherein said indole is 5,6-dihydroxyindole.

3. The process of claim 1 wherein said indole is selected from the group consisting of 2-methyl-5,6-dihydroxyindole, 3-methyl-5,6-dihydroxyindole, 1-methyl-5,6-dihydroxyindole, 2,3-dimethyl-5,6-dihydroxyindole and 5-methoxy-6-hydroxyindole.

4. The process of claim 1 wherein said pH regulating agent containing said components (A) and (B) is present in an amount ranging from $5 \times 10^{-3}$ to $50 \times 10^{-3}$ moles per 100 g of dyeing composition.

5. The process of claim 1 wherein the pH of said aqueous medium ranges from 7 to 9.

6. A composition for dyeing keratinous fibers comprising an aqueous medium containing a dyeing agent consisting of an indole having the formula (I)

wherein
$R_1$, $R_2$, $R_3$ and $R_4$, each independently, represent hydrogen or $C_1$–$C_4$ lower alkyl with the proviso that $R_1$, $R_2$ and $R_3$ represent hydrogen when $R_4$ represents alkyl and a pH-regulating agent present in an amount sufficient to adjust the pH of said composition to a $pH_C$ value ranging from 5 to 10, said pH-regulating agent containing two components (A) and (B), said component (A) being triethanolamine and said component (B) being a pH-regulating agent having a dissociation constant, $pK_{CB}$, in an aqueous solution at 25° C., of $2 < pK_{CB} \leq pH_C$, the weight ratio of said component (A) to said component (B) being greater than 1 and the molar ratio of said component (A) to said component (B) being greater than or equal to 2 and less than 15.

7. The composition of claim 6 wherein said indole is 5,6-dihydroxyindole.

8. The composition of claim 6 wherein said indole is selected from the group consisting of 2-methyl-5,6-dihydroxyindole, 3-methyl-5,6-dihydroxyindole, 1-methyl-5,6-dihydroxyindole, 2,3-dimethyl-5,6-dihydroxyindole and 5-methoxy-6-hydroxyindole.

9. The composition of claim 6 wherein said indole is present in an amount ranging from 0.01 to 5 percent by weight based on the total weight of said composition.

10. The composition of claim 6 wherein said indole is present in an amount ranging from 0.2 to 1 percent by weight based on the total weight of said composition.

11. The composition of claim 6 which includes a solvent in an amount ranging from 0.5 to 50 percent by weight, said solvent being selected from the group consisting of a $C_1$–$C_4$ lower alcohol, ethylene glycol, propylene glycol, ethylene glycol monomethyl ether, ethylene glycol monoethyl ether, ethylene glycol monobutyl ether, ethylene glycol monoethyl ether acetate, propylene glycol monomethyl ether, dipropylene glycol monomethyl ether and methyl lactate.

12. The composition of claim 11 wherein said solvent is present in an amount ranging from 2 to 20 percent.

13. The composition of claim 6 which also includes a thickening agent present in an amount ranging from 0.1 to 5 percent by weight based on the total weight of said composition.

14. The composition of claim which also includes a thickening agent present in an amount ranging from 0.5 to 3 percent by weight based on the total weight of said composition.

15. The composition of claim 6 which also includes at least one of a cationic, nonionic, anionic or amphoteric surfactant, or a mixture thereof, in an amount ranging from 0.1 to 50 percent by weight based on the total weight of said composition.

16. A process for dyeing keratinous fibers consisting of applying to said fibers the dye composition of claim 6 in an amount effective to dye said fibers, permitting said composition to remain in contact with said fibers for a period of time ranging from 1 to 40 minutes and rinsing said fibers.

17. A process for dyeing keratinous fibers consisting of applying to said fibers several times and successively the dye composition of claim 6.

* * * * *